(12) United States Patent
Nowak et al.

(10) Patent No.: US 10,207,090 B2
(45) Date of Patent: Feb. 19, 2019

(54) ADVANCED CERVICAL RIPENING SYSTEM

(71) Applicant: The Board of Regents of the University of Texas System, Austin, TX (US)

(72) Inventors: Brent M. Nowak, San Antonio, TX (US); Leonid Bunegin, San Antonio, TX (US); Pamela G. Ferguson, San Antonio, TX (US)

(73) Assignee: Board of Regents of the University of Texas System, Austin, TX (US)

( * ) Notice: Subject to any disclaimer, the term of this patent is extended or adjusted under 35 U.S.C. 154(b) by 816 days.

(21) Appl. No.: 14/387,931

(22) PCT Filed: Mar. 26, 2013

(86) PCT No.: PCT/US2013/033845
§ 371 (c)(1),
(2) Date: Sep. 25, 2014

(87) PCT Pub. No.: WO2013/148657
PCT Pub. Date: Oct. 3, 2013

(65) Prior Publication Data
US 2015/0045809 A1    Feb. 12, 2015

Related U.S. Application Data

(60) Provisional application No. 61/616,790, filed on Mar. 28, 2012.

(51) Int. Cl.
*A61B 17/42* (2006.01)
*A61B 17/46* (2006.01)
(Continued)

(52) U.S. Cl.
CPC ............. *A61M 29/02* (2013.01); *A61B 17/42* (2013.01); *A61B 2017/00557* (2013.01); *A61B 2017/4225* (2013.01)

(58) Field of Classification Search
CPC ............. A61M 29/02; A61M 25/1011; A61M 25/1002; A61M 25/0108; A61M 25/10;
(Continued)

(56) References Cited

U.S. PATENT DOCUMENTS 4,018,230 A    4/1977 Ochiai et al.
4,693,704 A    9/1987 Ogita
(Continued)

OTHER PUBLICATIONS

International Search Report/Written Opinion for PCT Application No. PCT/US2013/033845 dated Aug. 19, 2013.
(Continued)

*Primary Examiner* — Jonathan Miles
*Assistant Examiner* — Mohamed Gabr
(74) *Attorney, Agent, or Firm* — Meyertons, Hood, Kivlin, Kowert & Goetzel, P.C.

(57) ABSTRACT

Traditional and existing methods of cervical ripening employ a Foley Bulb designed for and typically used in bladder procedures. Consequently, the application to the cervix is sub-optimal. The described device resolves this and related limitations. The device includes a balloon that has been designed to accommodate the cervix geometry, and which can adapt to normal differences in the individual. Further improvements are attained by the use of a supporting device which couples the cervix ripening device to the individual.

9 Claims, 5 Drawing Sheets

(51) Int. Cl.
*A61D 1/10* (2006.01)
*A61M 29/02* (2006.01)
*A61B 17/00* (2006.01)

(58) Field of Classification Search
CPC ........ A61M 25/1018; A61M 25/10181; A61M 25/10182; A61M 25/10184; A61M 2210/1433; A61M 2210/14; A61M 2210/145; A61M 2210/1475; A61M 31/00; A61B 17/42; A61B 17/0218; A61B 2017/00557; A61B 2017/4225; A61B 2017/00544; A61B 2017/22054; A61B 2017/22061; A61B 2017/22062; A61B 1/32; A61B 2562/247; A61B 5/435; A61F 5/4553

See application file for complete search history.

(56) References Cited

U.S. PATENT DOCUMENTS

| | | | |
|---|---|---|---|
| 5,209,754 A | 5/1993 | Ahluwalia | |
| 5,947,991 A * | 9/1999 | Cowan | A61M 25/1002 604/103.07 |
| 6,110,200 A * | 8/2000 | Hinnenkamp | A61F 2/2496 33/512 |
| 2001/0018577 A1 | 8/2001 | Fitzpatrick et al. | |
| 2004/0116955 A1* | 6/2004 | Foltz | A61M 25/1011 606/193 |
| 2004/0127931 A1 | 7/2004 | Kincaid et al. | |
| 2004/0153116 A1 | 8/2004 | Nobles et al. | |
| 2006/0058831 A1 | 3/2006 | Atad | |
| 2006/0064038 A1* | 3/2006 | Omata | A61B 5/103 600/587 |
| 2007/0156067 A1* | 7/2007 | Dubey | A61B 5/1076 600/588 |
| 2007/0288051 A1* | 12/2007 | Beyer | A61M 29/02 606/193 |
| 2008/0058604 A1 | 3/2008 | Sorensen | |
| 2008/0319472 A1 | 12/2008 | Shelley | |
| 2009/0192542 A1 | 7/2009 | Harter | |
| 2009/0204099 A1 | 8/2009 | Feloney | |
| 2012/0130359 A1* | 5/2012 | Turovskiy | A61B 18/02 606/21 |

OTHER PUBLICATIONS

International Preliminary Report on Patentability for PCT Application No. PCT/US2013/033845 dated Oct. 1, 2014.
Atad et al. "A randomized comparison of prostaglandin E2 oxytocin, and the double-balloon device in inducing labor" Obstetrics & Gynecology, vol. 87, Issue 2, Feb. 1996, pp. 223-227.
Atad et al. "Ripening and Dilation of the Unfavorable Cervix for Induction of Labour by a Double Balloon Device: Experience with 250 Cases" British Journal of Obstetrics and Gynaecology Jan. 1997, vol. 104, pp. 29-32.
Karjane et al. "Induction of Labor Using a Foley Balloon, With and Without Extra-Amniotic Saline Infusion" Obstetrics & Gynecology, Feb. 2006—vol. 107—Issue 2, Part 1—pp. 234-239.
Levy et al. "A randomized trial comparing a 30-mL and an 80-mL Foley catheter balloon for preinduction cervical ripening" American Journal of Obstetrics & Gynecology, Nov. 2004, vol. 191, Issue 5, pp. 1632-1636.
Sherman et al. "Ripening of the Unfavorable Cervix With Extraamniotic Catheter Balloon: Clinical Experience and Review" Obstetrical & Gynecological Survey: Oct. 1996—vol. 51—Issue 10—pp. 621-627.

* cited by examiner

ADVANCED CERVICAL RIPENING SYSTEM

BACKGROUND OF THE INVENTION

1. Field of the Invention

The invention generally relates to cervical ripening devices and methods.

2. Description of the Relevant Art

Cervical ripening refers to the effacement or thinning of the cervix followed by dilation in preparation for the birthing process. Critical factors in the initiation of the ripening process include release of enzymes, hormonal factors, and local pressure on the internal os of the cervix as a result of the fetus' head following decent. When the progression of cervical ripening is slow or is not naturally initiated, stimulation by insertion and inflation of a balloon catheter to apply additional local has been shown to be effective.

Current methodology utilizes a Foley urinary catheter that is inserted into the cervical os and inflated to 50 to 80 ml with saline solution. The resulting spherical balloon is 5 to 6 cm in diameter. The area in contact with the internal os is roughly 30 to 45 $cm^2$ with the locally applied pressure a function of the cosine of the angle between the axis of the cervical channel and the point of contact by the balloon. The addition of approximately 1 Kg to the distal end of the Foley catheter has improved the ripening process substantially.

Several problems with the Foley catheter approach to cervical ripening are evident. Since the balloon is spherical, local pressure is not uniform over the internal os. This presents the potentiality that local release of hormonal and enzymatic factors are not uniformly induced in the cervix, thus, sub-optimally facilitating cervical ripening. Only the lower hemisphere of the balloon that is prescribed by the bisection of the catheter balloon by a plane perpendicular to the catheter axis is in contact with the internal os. The upper hemisphere protrudes in to the uterus potentially applying elevated pressure to the head of the fetus. The tip of the Foley catheter presents addition protrusion in to the uterus potentially injuring the fetus. The added kilogram of weight is generally a liter bag of saline solution which is allowed to hang over the side of the bed. Significant discomforts to the patient and the potential of injury from inadvertent snagging of the bag are added complications with this method.

SUMMARY OF THE INVENTION

A cervical ripening device includes an elongated tube comprising a first end and a second end; a balloon coupled to the second end of the elongated tube; wherein the balloon has a shape and size that matches the shape of the internal os of the cervix of a subject having a fetus present in the subject's uterus; and a support device coupled to the elongated tube, wherein the support device is couplable to a portion of the subject. In one embodiment, the elongated tube comprises an outer tube and an inner tube, wherein fluid used to fill the balloon is passed through the inner tube into the balloon during use.

In one embodiment, the balloon is substantially disk shaped. The portion of the balloon in contact with the cervix may have a curvature that substantially matches the curvature of the internal os of the cervix when a fetus is present in the uterus. In one embodiment, the balloon comprises a first disk and a second disk coupled to the first disk at the outer edge, wherein the first disk includes a reinforced material and the second disk comprises a membrane that is inflatable during use.

The support device, in one embodiment, may include a band couplable to the subject's leg. The elongated tube may be variably positionable with respect to the support device to alter the pressure placed on the internal os of the subject's cervix. In one embodiment, the support device is in the form of a pubic saddle that includes a first support member and a second support member coupled to each other. The first support member and the second support member couple to the pubic bone region of the subject and provide an outward force against the balloon during use. In an embodiment, the outward force applied on the balloon is altered by adjusting the position of the elongated tube with respect to the support device. The outward force applied to the balloon may be altered by adjusting a threaded collar engaged to threading on the elongated tube to adjust the position of the elongated tube with respect to the cervix.

In an embodiment, a method of inducing dilation of the cervix of a subject includes placing at least a portion of a cervical ripening device into the cervix of the subject, coupling the support device to the subject; inflating the balloon, wherein the balloon is positioned against the internal os of the cervix when inflated; and applying pressure to the cervix by moving the elongated tube away from the cervix.

In an embodiment, the cervical ripening device may be positioned by placing an insertion device into the cervix of the subject, and inserting at least a portion of the cervical ripening device through the insertion device into the cervix of the subject.

In an embodiment, applying pressure to the cervix includes adjusting a threaded collar engaged to threading on the elongated tube to adjust the position of the elongated tube with respect to the cervix.

A kit for of inducing dilation of the cervix of a subject may includes a cervical ripening device, an inserter for use in placing the cervical ripening device into the cervix of the subject; and one or more syringes for injecting a fluid into the balloon during use.

BRIEF DESCRIPTION OF THE DRAWINGS

Advantages of the present invention will become apparent to those skilled in the art with the benefit of the following detailed description of embodiments and upon reference to the accompanying drawings in which.

Figure 1:
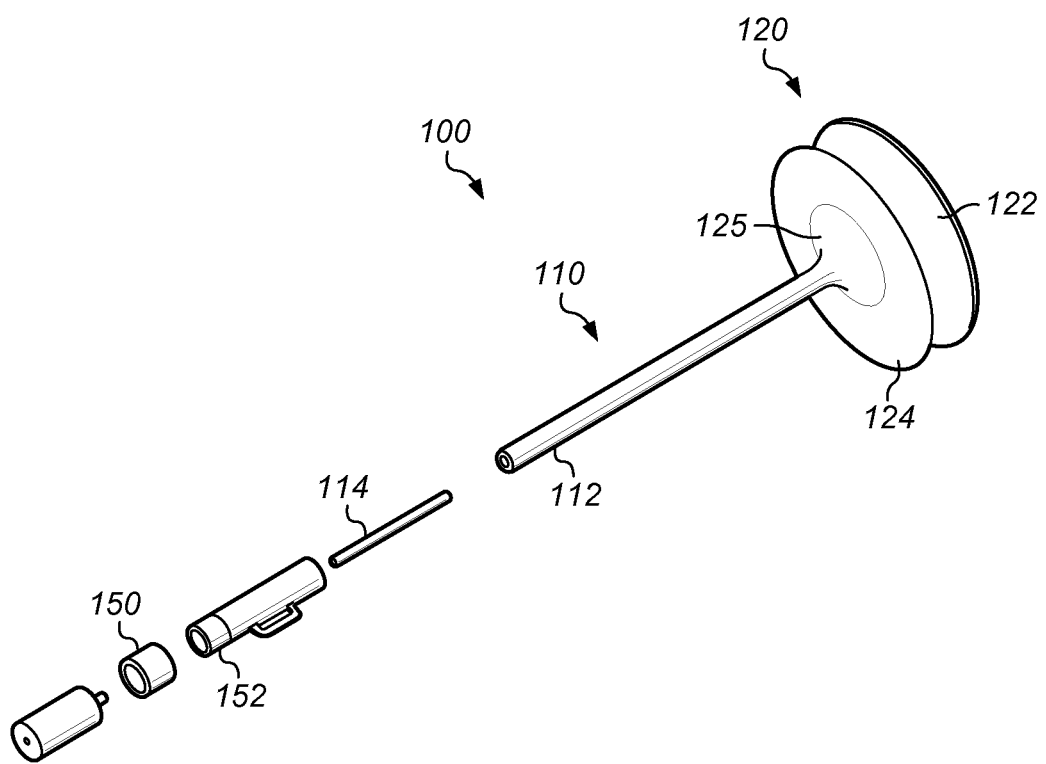
FIG. 1 depicts a projection view of an embodiment of an elongated tube of a cervical ripening device.

While the invention may be susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION OF THE PREFERRED EMBODIMENTS

It is to be understood the present invention is not limited to particular devices or methods, which may, of course, vary.

It is also to be understood that the terminology used herein is for the purpose of describing particular embodiments only, and is not intended to be limiting. As used in this specification and the appended claims, the singular forms "a", "an", and "the" include singular and plural referents unless the content clearly dictates otherwise. Furthermore, the word "may" is used throughout this application in a permissive sense (i.e., having the potential to, being able to), not in a mandatory sense (i.e., must). The term "include," and derivations thereof, mean "including, but not limited to." The term "coupled" means directly or indirectly connected.

To remedy at least some of the problems associated with using a traditional Foley catheter to induce cervical dilation, the following parameters were identified. A cervical ripening device should:

1. have an inflatable balloon having a conformation similar to that of the cervix internal os;
2. apply a uniform distribution of force over the contact area of the cervix internal os;
3. incorporate an internal channel for infusion of sterile saline;
4. be capable of deployment of the catheter through an insertion device; and
5. utilize the elasticity of the catheter in combination with a support device to apply and fix traction onto the cervix internal os in a measurable and consistent fashion.

The curvature of the cervix internal os surface, however, is not uniform but varies to approximate the curvature of the fetal head. In the frontal or coronal plane the radius of curvature is approximately 4.5 cm, with the lateral or sagittal plane curvature average of 5.6 cm (5.0 cm radius posterior to the ear and 5.8 anterior to the ear). The average radius of curvature of the cervix internal os is roughly 5 cm.

In the current usage of the Foley catheter for initiation of cervical ripening, a balloon is inflated with 60 to 80 ml of sterile saline. The infused volume produces a spherical balloon having a diameter between 5 and 6 cm. As noted above, however, the balloon is spherical and local pressure is not uniform over the cervix internal os due to the differences in curvature.

To remedy the non-uniform shape of the cervix internal os, a balloon was designed to better match the known curvature of the internal os when a fetus is present. In one embodiment, a balloon is formed from two silicone disks as shown in FIG. 1. A cervical ripening device 100 includes an elongated tube 110 and a balloon 120 that is formed from two silicone disks 122 and 124. The balloon 120 includes, in one embodiment, two 5.5 cm diameter concave silicone disks 122 and 124 having a radius of curvature of 5 cm. The disks may generally have a diameter ranging from about 1 cm to about 10 cm and a radius of curvature of between about 1 cm to about 10 cm.

Upper disk 122 may be fiber reinforced silicone. The fiber may limit expansion of the upper disk, helping to define the shape and size of the balloon. Lower disk 124 is composed of a silicone membrane that may be expand when a fluid is introduced into the balloon. During use lower disk 124 contacts the cervix internal os of the patient. The fluid in the balloon helps the lower disk to conform with the shape of the subjects cervix. The disks may be bonded at the outer edge to form an inflatable cavity having a volume of approximately 2-4 ml. Openings 125 on the central axis of the disks couple the balloon to the elongated tube 110. The disks are bonded to elongated tube 110 such that the upper disk 122 is coplanar with the tip of the elongated tube and the lower (membrane) disk 124 is bonded 1 to 2 mm below the upper disk.

The area of the cervix internal os in contact with the inflated disk balloon 120 varies from about 15 $cm^2$ to about 40 $cm^2$ depending on the size and radius of curvature of the disks. In an embodiment, when the disks have a diameter of 5.5 cm and a radius of curvature of 5 cm, the area of internal os contact is about 23.5 $cm^2$. An advantage of the above described balloon, is that the balloon can adapt and/or form to match both the specific shape of the internal os and/or the infant's head.

Elongated tube 110 may be formed from a flexible material that has a stiffness suitable for easy insertion, a low resistance internal channel for saline injection, and sufficient wall thickness for incorporation of a balloon inflation channel. In one embodiment, a 0.25 in outside diameter silicone tube with 0.063 in wall thickness was selected as the elongated tube 110 for the cervical ripening device. Elongated tube 110 may have a length of about 20 cm to about 50 cm long. The tube should have a length sufficient to allow the tube to extend from the subjects cervix to a position proximate to the legs of the patient.

In one embodiment, elongated tube 110 is composed of an outer tube 112 and an inner tube 114. Inner tube 114 is used for inflation of balloon 120. Inner tube 114 is used to inject a fluid into the balloon, is of low resistance and allows easy infusion of aqueous fluids. In one embodiment, saline is injected into the balloon to inflate the balloon during use. Outer tube may be used for injection of an amniotic saline infusion.

A support device may be coupled to the elongated tube. The support device is couplable to a portion of the subject to secure the catheter to the subject. The support device also is configured to allow the forces applied to the balloon to be varied by adjusting the position of the elongated tube with respect to the support device.

Figure 2:
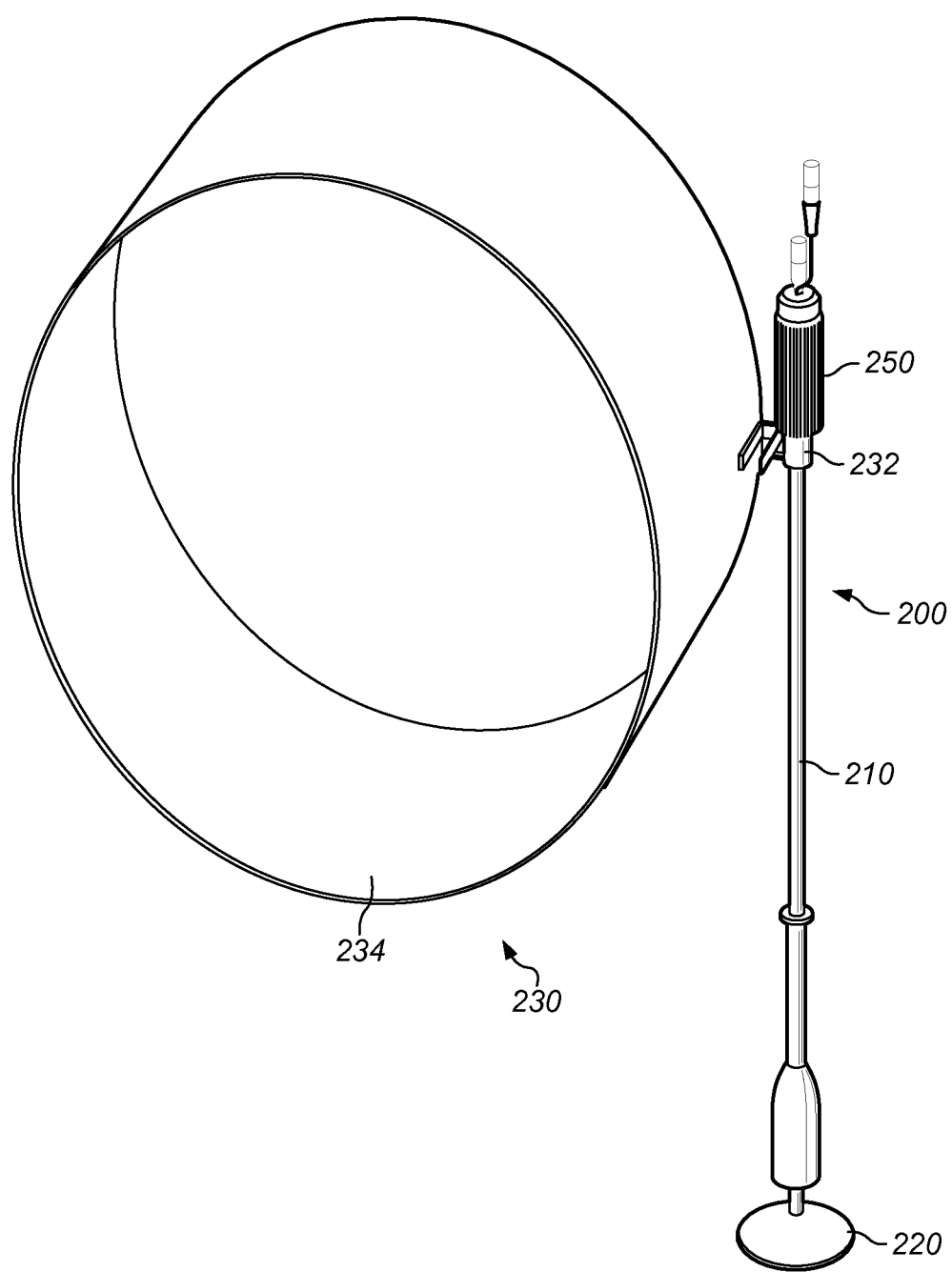
FIG. 2 depicts a projection view of an embodiment of a cervical ripening device having a support device.

An embodiment of a cervical ripening device having a support device is depicted in FIG. 2. Cervical ripening device 200 includes an elongated tube 210 and a balloon 220 coupled to the elongated tube 210. A support device 230 is coupled to elongated tube 210. Support device 230 is, in one embodiment, includes a band 234 couplable to the subject's leg. A coupling 232 couples band 234 to elongated tube 210.

Support device 230 inhibits dislodgment of the cervical ripening device from the subject. Support device also provides a stable anchor from which tension can be applied to the balloon. In the embodiment depicted in FIG. 2, a threaded collar 250 is coupled to external threading (not shown, depicted in FIG. 1 as elements 150 and 152) of elongated member 210. Turning threaded collar 250 in a predetermined direction causes elongated tube 210 to move in a direction away from coupling 232. Movement of elongated tube 210 away from the coupling 232 creates tension on balloon 210 during use. In one example, it was determined that the application of 9.8N (1 Kg×9.8 m/sec$^2$) of tension to the cervical ripening device tube results in a calculated uniform pressure distribution of around 0.41 N/cm$^2$ to the cervix internal os. In one embodiment, calibration marks may be formed on the elongated tube to allow the user to estimate the pressure applied to the cervix by the device.

Figure 3:
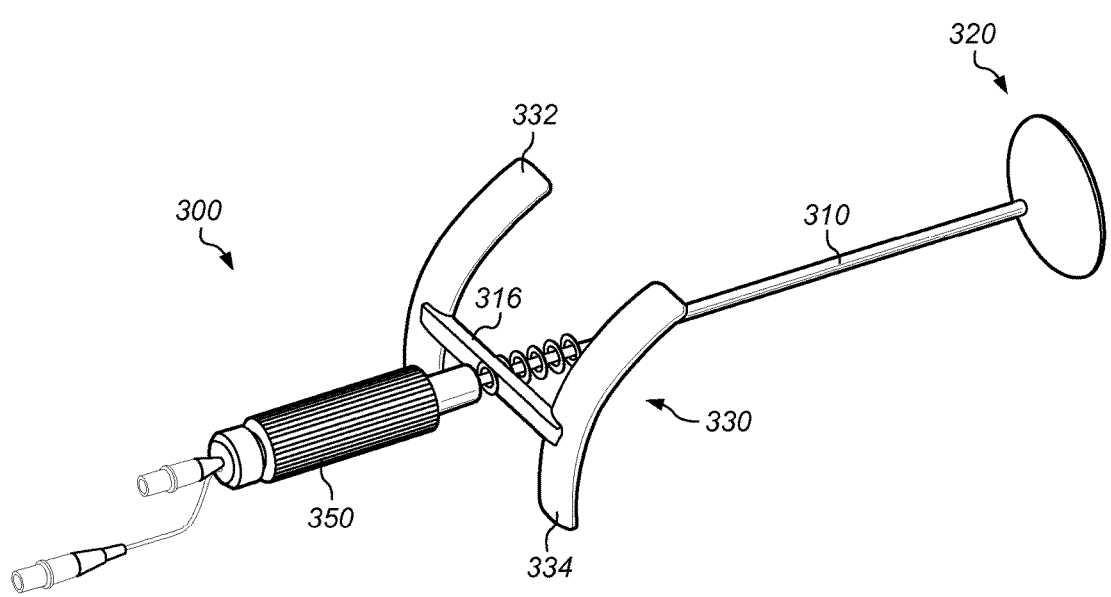
FIG. 3 depicts a projection view of an alternate embodiment of a cervical ripening device having a support device.

In an alternate embodiment, a support device 320 may include a pubic saddle that is used as a support device 330, as depicted in FIG. 3. Pubic saddle includes a first support member 332 and a second support member 334 coupled to each other through coupling support 336. First support member 332 and second support member 334 have a shape which is complementary with the general shape and size of the pubic bone region. During use, first support member 332 and second support member 334 are coupled to the pubic bone region of the subject and balloon 320 is inserted into the cervix. Elongated tube 310 is fixedly coupled to coupling support 336. During use, pressure may be increased on the cervix by moving the elongated tube away from the coupling support. Coupling support may engage elongated tube using a threaded collar 350 coupled to threads on the elongated tube. Calibrations on the collar specify may be used to estimate the tension on the cervix. The pubic saddle design for the support device allows easy access to the vaginal canal.

Figure 4:
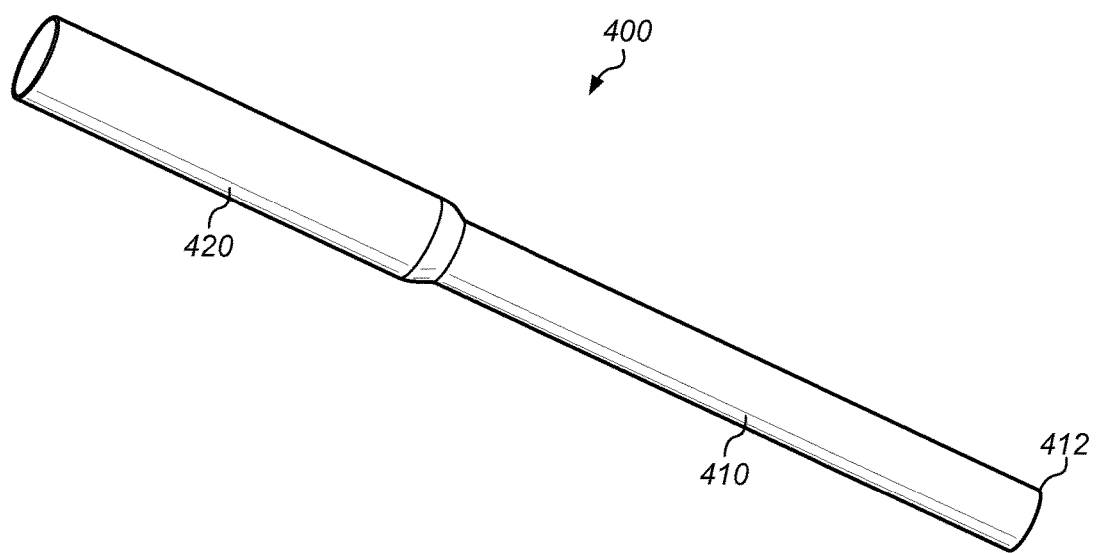
FIG. 4 depicts a projection view of an insertion device.

FIG. 4 depicts an insertion device 400 used to properly position the cervical ripening device in the proper position. In one embodiment, insert is formed from a polymeric tube with end designs that will provide easy insertion while minimizing potential injury. In one embodiment, insertion device 400 is composed of a polypropylene material, similar to the material that is used to facilitate tampon insertion. Insertion device 400 may include an insertion tube 410 and receiving tube 420. During use, insertion device 400 is placed in the cervix of the subject such that end 412 of insertion tube 410 enters the uterus of the subject. A cervical dilator device, such as the devices described herein, may be positioned in the receiving tube 420 of the inserter and passed through insertion tube 410, such that the balloon of the cervical dilator device is positioned in the uterus. The use of an inserter allows easy insertion and positioning of the cervical dilator device. In some embodiments, marking on the insertion device may correspond to markings on the cervical dilator device to allow the user to determine how far the device has been inserted into the subject.

In an embodiment, dilation of the cervix of a subject may be accomplished by placing the devices described herein through the cervix of the subject such that the balloon is in the uterus of the subject. An insertion device may be used to assist positioning of the cervical ripening device in the subject. Once positioned, a support device of the cervix dilator device may be coupled to the subject. The balloon is then inflated by passing fluid through the elongated tube. The inflated balloon is thus positioned against the internal os of the cervix. To improve dilation of the cervix, the elongated tube is moved in a direction away from the cervix. This "pulls" the balloon against the cervix, creating an environment that encourages dilation of the cervix. In one embodiment, the cervical ripening device includes a threaded collar which is coupled to threading on the elongated tube. Adjustment of the threaded collar alters the position of the elongated tube with respect to the support and therefore with respect to the cervix. In this manner, the amount of pressure placed against the cervix by the balloon may be altered.

In one embodiment, the device may be placed into the cervix with speculum or by digital exam. The catheter may be placed with the speculum or by digital guidance into the cervical os and advancing the catheter until it is in the cervix about 2 cms. After the catheter is in place, the guide is removed and the catheter is held in position. Using a syringe with sterile water, water is placed into the appropriate tube while the catheter is held in place. Once the balloon is inflated and determined to be at the internal os, the catheter is then attached to the supporting device and the desired traction is created.

Figure 5:
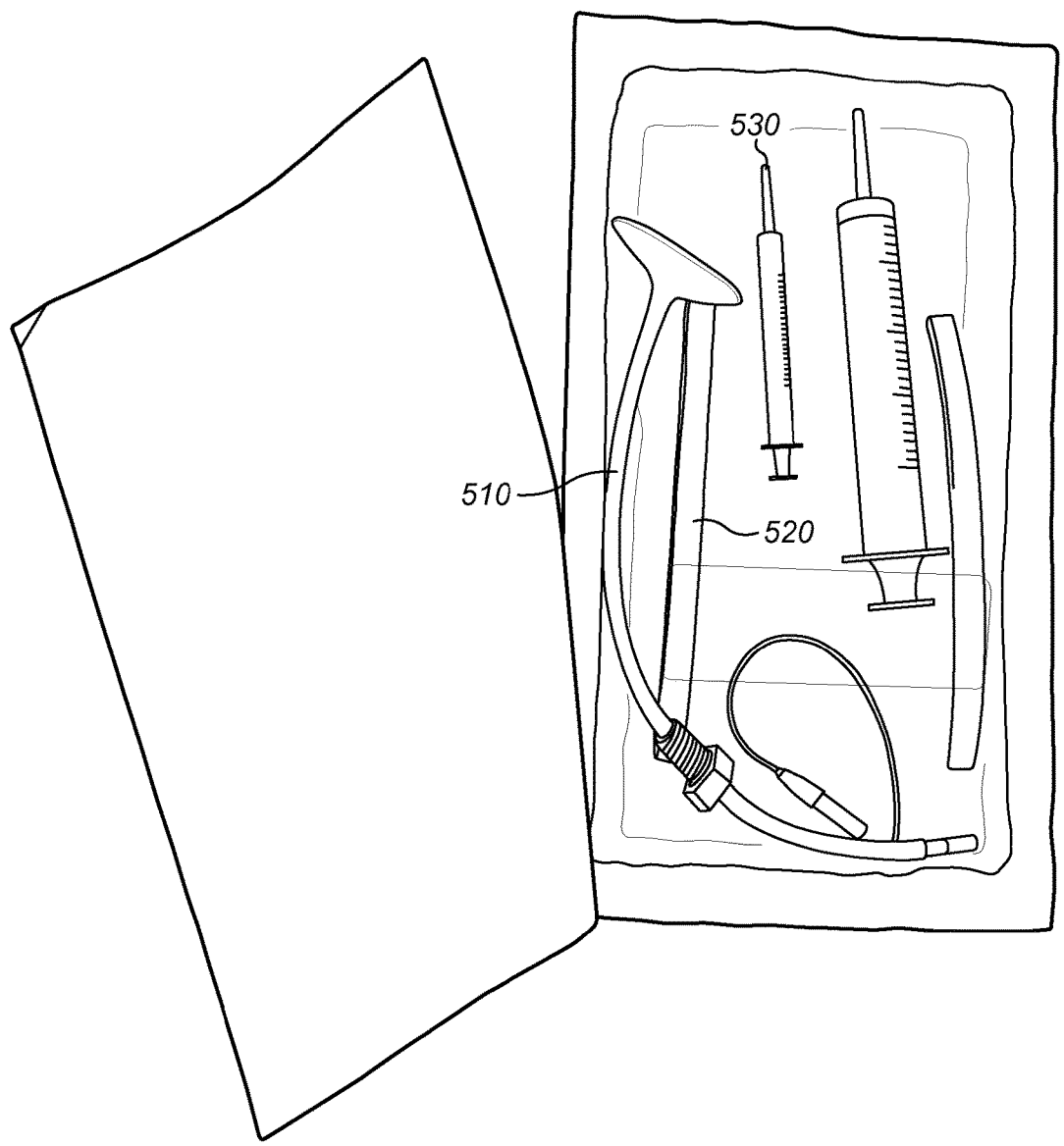
FIG. 5 depicts a cervical ripening kit.

FIG. 5 depicts a kit that includes components that are used to induce dilation of the cervix of a subject. Kit 500 includes a cervical ripening device 510, a support device 520, and one or more syringes 530 used to inject fluids into the balloon. An inserter (not shown) may also be included with the kit.

While the primary use of the device is for cervical ripening, the device may also be used for other in utero procedures. For example, the device may be used to withdraw body fluids from within the womb, through the same aperture that is used to inject the amniotic saline infusion. Furthermore, along with amniotic saline infusion, medications may also be injected into the uterus through the same tube. In some embodiments, the device may include tow or more inlet/outlet ports that extend into the uterus when the device is positioned in the subject.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A cervical ripening device comprising:
   an elongated tube comprising a first end configured to be positioned within a subject's body, a second end configured to be positioned outside the patient's body, the elongated tube further comprising an outer tube and an inner tube;
   a threaded collar attached to an external threading on the second end of the elongated tube; and
   a balloon coupled to the first end of the elongated tube; wherein the balloon has a shape and size that matches the shape of the internal os of the cervix of a subject having a fetus present in the subject's uterus;
   wherein the balloon is composed of a first disk and a second disk, wherein the first disk and the second disk are connected to each other at an outer edge to form a single inflatable cavity, wherein the first disk comprises a reinforced material that limits the expansion of the first disk, and the second disk comprises a membrane that is expandable during use; and
   wherein the cervical ripening device further comprises a support device slideably coupled to the elongated tube between the threaded collar and the balloon, wherein the support device is configured to couple to the subject outside of the subject's body and provide a pulling force against the balloon during use;
   wherein rotation of the threaded collar in a predetermined position along the external threading of the elongated tube moved the balloon relative to the support device to alter the pulling force applied to the balloon.

2. The device of claim 1, wherein the second disk has a curvature that substantially matches the curvature of the internal os of the cervix when a fetus is present in the uterus.

3. The device of claim 1, wherein the support device comprises a band couplable to the subject's leg.

4. The device of claim 1, wherein the support device comprises a first support member and a second support member coupled to each other, wherein the first support member and the second support member are capable of coupling to the pubic bone region of the subject.

5. A method of inducing dilation of the cervix of a subject comprising:
   placing at least a portion of the cervical ripening device according to claim 1 into the cervix of the subject;
   coupling the support device to the subject;
   inflating the balloon, wherein the balloon is positioned against the internal os of the cervix when inflated, wherein fluid used to fill the balloon is passed through the inner tube and into the first disk and the second disk substantially simultaneously to inflate the balloon;
   applying pressure to the cervix by moving the elongated tube away from the cervix.

6. The method of claim 5, further comprising placing an insertion device into the cervix of the subject, and inserting at least a portion of the cervical ripening device through the insertion device into the cervix of the subject.

7. The method of claim 5, wherein the balloon is inflated with a saline solution.

8. The method of claim 5, wherein applying pressure comprises adjusting a threaded collar engaged to threading on the elongated tube to adjust the position of the elongated tube with respect to the cervix.

9. A kit for of inducing dilation of the cervix of a subject comprising:
   the cervical ripening device according to claim 1;
   an inserter for use in placing the cervical ripening device into the cervix of the subject;
   one or more syringes for injecting a fluid into the balloon during use.

* * * * *